US011999653B2

(12) United States Patent
Deng et al.

(10) Patent No.: US 11,999,653 B2
(45) Date of Patent: Jun. 4, 2024

(54) HIGH LIQUIDUS VISCOSITY BIOACTIVE GLASS

(71) Applicant: CORNING INCORPORATED, Corning, NY (US)

(72) Inventors: Huayun Deng, Painted Post, NY (US); Qiang Fu, Painted Post, NY (US); John Christopher Mauro, Boalsburg, PA (US); Michael Joshua Snyder, Almond, NY (US)

(73) Assignee: CORNING INCORPORATED, Corning, NY (US)

( * ) Notice: Subject to any disclaimer, the term of this patent is extended or adjusted under 35 U.S.C. 154(b) by 5 days.

(21) Appl. No.: 17/832,208

(22) Filed: Jun. 3, 2022

(65) Prior Publication Data
US 2022/0298058 A1 Sep. 22, 2022

Related U.S. Application Data

(62) Division of application No. 16/202,952, filed on Nov. 28, 2018, now Pat. No. 11,384,009.

(60) Provisional application No. 62/591,446, filed on Nov. 28, 2017.

(51) Int. Cl.
*C03C 3/097* (2006.01)
*A61K 33/42* (2006.01)
*C03C 4/00* (2006.01)
*C03C 13/00* (2006.01)
*C03B 37/02* (2006.01)
*C03B 37/022* (2006.01)

(52) U.S. Cl.
CPC .............. *C03C 3/097* (2013.01); *A61K 33/42* (2013.01); *C03C 4/0014* (2013.01); *C03C 4/0021* (2013.01); *C03C 13/00* (2013.01); *C03B 37/02* (2013.01); *C03B 37/022* (2013.01); *C03C 2204/00* (2013.01); *C03C 2213/00* (2013.01); *C03C 2213/02* (2013.01)

(58) Field of Classification Search
None
See application file for complete search history.

(56) References Cited

U.S. PATENT DOCUMENTS

| | | |
|---|---|---|
| 2,532,386 A | 12/1950 | Armistead |
| 2,978,339 A | 4/1961 | Veatch et al. |
| 2,987,339 A | 6/1961 | Kaplan et al. |
| 3,323,888 A | 6/1967 | Searight et al. |
| 3,778,335 A | 12/1973 | Boyd |
| 3,790,430 A | 2/1974 | Mochel |
| 4,083,727 A | 4/1978 | Andrus et al. |
| 4,084,972 A | 4/1978 | Andrus et al. |
| 4,126,437 A | 11/1978 | O'Horo |
| 4,140,645 A | 2/1979 | Beall et al. |
| 4,233,169 A | 11/1980 | Beall et al. |
| 4,323,056 A | 4/1982 | Borrelli et al. |
| 4,340,693 A | 7/1982 | Drake et al. |
| 4,391,646 A | 7/1983 | Howell |
| 4,889,707 A | 12/1989 | Day et al. |
| 5,024,973 A | 6/1991 | Kondo et al. |
| 5,081,394 A | 1/1992 | Morishita et al. |
| 5,153,070 A | 10/1992 | Andrus et al. |
| 5,217,928 A | 6/1993 | Goetz et al. |
| 5,252,523 A | 10/1993 | Beall et al. |
| 5,648,124 A | 7/1997 | Sutor |
| 5,674,790 A | 10/1997 | Araujo |
| 5,849,816 A | 12/1998 | Suskind et al. |
| 5,876,452 A | 3/1999 | Athanasiou et al. |
| 6,034,014 A | 3/2000 | Rapp et al. |
| 6,214,471 B1 | 4/2001 | Beall et al. |
| 6,254,981 B1 | 7/2001 | Castle |
| 6,280,863 B1 | 8/2001 | Frank et al. |
| 6,328,990 B1 | 12/2001 | Ducheyne et al. |
| 6,338,751 B1 | 1/2002 | Litkowski et al. |
| 6,506,399 B2 | 1/2003 | Donovan |
| 6,514,892 B1 | 2/2003 | Kasai et al. |
| 6,802,894 B2 | 10/2004 | Brodkin et al. |
| 6,838,171 B2 | 1/2005 | Nomura |

(Continued)

FOREIGN PATENT DOCUMENTS

| | | |
|---|---|---|
| CA | 2577628 A1 | 3/2006 |
| CA | 2926665 A1 | 5/2015 |

(Continued)

OTHER PUBLICATIONS

Gorustovich et al., "Osteoconductivity of strontium-doped bioactive glass particles: A histomorphometric study in rats," J Biomed Materials Res. Part A (2010) 92A: pp. 232-237.
Graham, "High-Sensitivity Manetization Measurements", J. Mater. Sci. Technol., vol. 16, No. 2, 2000, p. 97-101.
Gunter et al., "Calcium pectinate gel beads obtained from callus cultures pectins aspromising systems for colon-argeted drug delivery," Carbohydrate Polymers, 2016, pp. 490-499.
Gy, "Ion Exchange for Glass Strengthening," Mater Sci EHG B, 2008, 149: 159-165.

(Continued)

*Primary Examiner* — Celeste A Roney
(74) *Attorney, Agent, or Firm* — Travis B. Gasa

(57) ABSTRACT

Methods of making a bioactive glass fiber include forming a melt of a glass composition including: 50 to 70% $SiO_2$; 0.1 to 10% $Al_2O_3$, 5 to 30% $Na_2O$, 0.1 to 15% $K_2O$, 0.1 to 15% MgO, 0.1 to 20% CaO, and 5 to 10% $P_2O_5$, based on a 100 wt % of the glass composition. The melt has a viscosity of from 200 Poise to 2,000 Poise. Methods include drawing the melt into a drawn glass fiber. Bioactive glass compositions include: 60 to 70% $SiO_2$; 15 to 30% $Na_2O$, 5 to 15% $K_2O$, 1 to 10% CaO, and 5 to 10% $P_2O_5$, based on a 100 wt % of the glass composition.

13 Claims, 2 Drawing Sheets

(56) References Cited

U.S. PATENT DOCUMENTS

| | | |
|---|---|---|
| 6,852,656 B1 | 2/2005 | La Greca et al. |
| 7,047,634 B2 | 5/2006 | Nakamura |
| 7,047,637 B2 | 5/2006 | Derochemont et al. |
| 7,166,548 B2 | 1/2007 | Apel et al. |
| 7,166,549 B2 | 1/2007 | Fechner et al. |
| 7,192,602 B2 | 3/2007 | Fechner et al. |
| 7,316,740 B2 | 1/2008 | Schweiger et al. |
| 7,597,900 B2 | 10/2009 | Zimmer et al. |
| 7,704,903 B2 | 4/2010 | Seneschal et al. |
| 7,709,027 B2 | 5/2010 | Fechner et al. |
| 7,905,115 B2 | 3/2011 | Raeke et al. |
| 7,914,874 B2 | 3/2011 | Henry et al. |
| 7,989,065 B2 | 8/2011 | Winstead et al. |
| 8,080,490 B2 | 12/2011 | Fechner et al. |
| 8,173,154 B2 | 5/2012 | Jung et al. |
| 8,637,300 B2 | 1/2014 | Ruf et al. |
| 9,056,045 B2 | 6/2015 | Hughes et al. |
| 9,084,844 B2 | 7/2015 | Vallittu |
| 9,101,439 B2 | 8/2015 | Ritzberger et al. |
| 9,168,272 B2 | 10/2015 | Hill et al. |
| 9,232,989 B2 | 1/2016 | Ritzberger et al. |
| 9,238,044 B2 | 1/2016 | Da Fonte Ferreira et al. |
| 9,241,879 B2 | 1/2016 | Castillo |
| 9,326,995 B2 | 5/2016 | Stucky et al. |
| 9,371,249 B2 | 6/2016 | Ritzberger et al. |
| 9,498,459 B2 | 11/2016 | Pomrink et al. |
| 9,622,483 B2 | 4/2017 | Bookbinder et al. |
| 9,688,567 B2 | 6/2017 | Rampf et al. |
| 9,700,391 B2 | 7/2017 | Kounga et al. |
| 9,701,573 B2 | 7/2017 | Beall et al. |
| 9,731,995 B2 | 8/2017 | Kim et al. |
| 2004/0120908 A1 | 6/2004 | Cohen et al. |
| 2004/0166172 A1 | 8/2004 | Rosati et al. |
| 2004/0228905 A1 | 11/2004 | Greenspan et al. |
| 2005/0118236 A1 | 6/2005 | Qiu et al. |
| 2005/0142077 A1 | 6/2005 | Zimmer et al. |
| 2005/0158395 A1 | 7/2005 | Zimmermann et al. |
| 2005/0233888 A1 | 10/2005 | Seneschal et al. |
| 2006/0127427 A1 | 6/2006 | Vernice et al. |
| 2006/0292280 A1 | 12/2006 | Soper et al. |
| 2007/0122356 A1 | 5/2007 | Kessler et al. |
| 2007/0281033 A1 | 12/2007 | Rochat |
| 2008/0214428 A1 | 9/2008 | Orlich et al. |
| 2008/0233201 A1 | 9/2008 | Royere et al. |
| 2009/0208428 A1 | 8/2009 | Hill et al. |
| 2009/0258778 A1 | 10/2009 | Castillo |
| 2009/0324668 A1 | 12/2009 | Kangasniemi et al. |
| 2011/0008293 A1 | 1/2011 | Bhandari |
| 2011/0009254 A1 | 1/2011 | Schweiger et al. |
| 2011/0152057 A1 | 6/2011 | Qi |
| 2011/0165221 A1 | 7/2011 | Jung et al. |
| 2012/0020898 A1 | 1/2012 | Mandadi et al. |
| 2012/0065756 A1 | 3/2012 | Rubbert et al. |
| 2012/0135848 A1 | 5/2012 | Beall et al. |
| 2012/0317735 A1 | 12/2012 | Gonzales et al. |
| 2012/0321567 A1 | 12/2012 | Gonzales et al. |
| 2013/0011446 A1 | 1/2013 | Depaula |
| 2013/0266625 A1 | 10/2013 | Benita et al. |
| 2014/0000891 A1 | 1/2014 | Mahoney et al. |
| 2014/0026916 A1 | 1/2014 | Havens et al. |
| 2014/0135202 A1 | 5/2014 | Ritzberger et al. |
| 2014/0186274 A1 | 7/2014 | Hodgkinson |
| 2014/0193499 A1 | 7/2014 | Da Fonte Ferreira et al. |
| 2014/0212469 A1 | 7/2014 | Rahaman et al. |
| 2014/0219941 A1 | 8/2014 | Takekawa et al. |
| 2014/0228196 A1 | 8/2014 | Ritzberger et al. |
| 2014/0271913 A1 | 9/2014 | Pomrink et al. |
| 2014/0349831 A1 | 11/2014 | Cornejo et al. |
| 2014/0370464 A1 | 12/2014 | Kounga et al. |
| 2015/0087493 A1 | 3/2015 | Ritzberger et al. |
| 2015/0104655 A1 | 4/2015 | Kim et al. |
| 2015/0231042 A1 | 8/2015 | Gonzales et al. |
| 2015/0239772 A1 | 8/2015 | Baker et al. |
| 2015/0265509 A1 | 9/2015 | Zhang et al. |
| 2015/0274581 A1 | 10/2015 | Beall et al. |
| 2015/0299031 A1 | 10/2015 | Ritzberger et al. |
| 2015/0374589 A1 | 12/2015 | Rampf et al. |
| 2016/0060159 A1 | 3/2016 | Kim et al. |
| 2016/0102010 A1 | 4/2016 | Beall et al. |
| 2016/0145567 A1 | 5/2016 | Henry et al. |
| 2016/0340239 A1 | 11/2016 | Propster et al. |
| 2017/0086877 A1 | 3/2017 | Moffarah et al. |
| 2017/0274118 A1 | 9/2017 | Nazhat et al. |
| 2017/0305782 A1* | 10/2017 | Li .................. C03C 3/087 |
| 2017/0340527 A1 | 11/2017 | Chang et al. |
| 2017/0340666 A1 | 11/2017 | Deng et al. |
| 2017/0341975 A1 | 11/2017 | Gross et al. |
| 2017/0342382 A1 | 11/2017 | Deng et al. |
| 2017/0342383 A1 | 11/2017 | Deng et al. |
| 2017/0349876 A1 | 12/2017 | Deng et al. |
| 2017/0354755 A1 | 12/2017 | Weinberger et al. |
| 2018/0343255 A1 | 11/2018 | Thibadeau et al. |
| 2019/0048318 A1 | 2/2019 | Deng et al. |
| 2019/0060523 A1 | 2/2019 | Bakry |

FOREIGN PATENT DOCUMENTS

| | | |
|---|---|---|
| CN | 1032265 A | 4/1989 |
| CN | 1054055 A | 8/1991 |
| CN | 1155844 A | 7/1997 |
| CN | 1213355 A | 4/1999 |
| CN | 1325291 A | 12/2001 |
| CN | 1615280 A | 5/2005 |
| CN | 1838936 A | 9/2006 |
| CN | 101018573 A | 8/2007 |
| CN | 101407373 A | 4/2009 |
| CN | 101500622 A | 8/2009 |
| CN | 101596326 A | 12/2009 |
| CN | 101704632 A | 5/2010 |
| CN | 101808955 A | 8/2010 |
| CN | 101938877 A | 1/2011 |
| CN | 102421716 A | 4/2012 |
| CN | 102430149 A | 5/2012 |
| CN | 102526797 A | 7/2012 |
| CN | 103172263 A | 6/2013 |
| CN | 103449725 A | 12/2013 |
| CN | 103930086 A | 7/2014 |
| CN | 103979796 A | 8/2014 |
| CN | 104039729 A | 9/2014 |
| CN | 104108883 A | 10/2014 |
| CN | 104379113 A | 2/2015 |
| CN | 104736126 A | 6/2015 |
| CN | 104876439 A | 9/2015 |
| CN | 105236745 A | 1/2016 |
| CN | 105819697 A | 8/2016 |
| CN | 107028770 A | 8/2017 |
| DE | 10214273 A1 | 10/2003 |
| DE | 102005026269 A1 | 12/2006 |
| EP | 0583791 A1 | 2/1994 |
| EP | 0885855 A2 | 12/1998 |
| EP | 0935526 A1 | 8/1999 |
| EP | 1116698 A1 | 7/2001 |
| EP | 1123072 A1 | 8/2001 |
| EP | 1233721 A1 | 8/2002 |
| EP | 1452496 A1 | 9/2004 |
| EP | 1580172 A2 | 9/2005 |
| EP | 1021148 B1 | 5/2008 |
| EP | 2868634 A1 | 5/2015 |
| EP | 3095436 A1 | 11/2016 |
| HU | 0302501 A2 | 1/2006 |
| HU | 0227595 B1 | 9/2011 |
| HU | 227595 B1 | 9/2011 |
| JP | 2983962 B2 | 11/1999 |
| JP | 2001-010843 A | 1/2001 |
| JP | 3306811 B2 | 7/2002 |
| JP | 2004-359754 A | 12/2004 |
| JP | 2005-053776 A | 3/2005 |
| JP | 2005-255517 A | 9/2005 |
| JP | 2007-001846 A | 1/2007 |
| JP | 2007-039269 A | 2/2007 |
| JP | 2015-504399 A | 2/2015 |
| JP | 2015-505786 A | 2/2015 |
| JP | 2015-509016 A | 3/2015 |
| JP | 2015-525180 A | 9/2015 |

(56) References Cited

FOREIGN PATENT DOCUMENTS

| KR | 10-2007-0081952 A | | 8/2007 | |
|---|---|---|---|---|
| KR | 10-0781952 B1 | | 12/2007 | |
| KR | 20130112433 | * | 4/2012 | ............ C03C 3/087 |
| KR | 20130112433 A | * | 4/2012 | ............ C03C 3/087 |
| KR | 10-2013-0112422 A | | 10/2013 | |
| KR | 10-2013-0112433 A | | 10/2013 | |
| WO | 87/07256 A1 | | 12/1987 | |
| WO | 91/12032 A1 | | 8/1991 | |
| WO | 97/18171 A1 | | 5/1997 | |
| WO | 97/27148 A1 | | 7/1997 | |
| WO | 97/27884 A1 | | 8/1997 | |
| WO | 98/08672 A1 | | 3/1998 | |
| WO | 98/15263 A2 | | 4/1998 | |
| WO | 99/62835 A1 | | 12/1999 | |
| WO | 00/15167 A1 | | 3/2000 | |
| WO | 01/34060 A1 | | 5/2001 | |
| WO | 2006/072394 A1 | | 7/2006 | |
| WO | 2007/022264 A2 | | 2/2007 | |
| WO | 2007/141978 A1 | | 12/2007 | |
| WO | 2008/000888 A2 | | 1/2008 | |
| WO | 2011/084572 A2 | | 7/2011 | |
| WO | 2011/141896 A1 | | 11/2011 | |
| WO | 2012/091201 A1 | | 7/2012 | |
| WO | 2012/137158 A1 | | 10/2012 | |
| WO | 2014/015240 A1 | | 1/2014 | |
| WO | 2014/052973 A1 | | 4/2014 | |
| WO | 2014/095198 A1 | | 6/2014 | |
| WO | 2014/159240 A1 | | 10/2014 | |
| WO | 2015/034860 A1 | | 3/2015 | |
| WO | 2015/123049 A1 | | 8/2015 | |
| WO | 2015/200017 A1 | | 12/2015 | |
| WO | 2017/205589 A1 | | 11/2017 | |

OTHER PUBLICATIONS

Han et al., "In Vivo Remineralization of Dentin Using an Agarose Hydrogel Biomimetic Mineralization System"; Nature, Scientific Reports; (2017); 9 pages.
Harianawala et al., "Biocompatibility of Zirconia", J Adv Med Deni Sci Res 4(3) 2016, pp. 35-39.
Hench; "Bioceramics", J. Am. Ceram. Soc., 81, (7), 1705-1728 (1998).
Hiorth et al., "Immersion Coating of Pellets With Calcium Pectinate and Chitosan"; International Journal of Pharmaceutics 308 (2006) 25-32.
Holand et al., "A Comparison of the Microstructure and Properties of the IPS Empresst2 and the IPS Empresst Glass-Ceramics"; J Biomed Mater Res (Appl Biomater), 2000, 53: 297-303.
Huang et al., "Kinetics and Mechanisms of the Conversion of Silicate (45S5), Borate and Borosilicate Glasses To Hydroxyapatite in Dilute Phosphate Solutions," J Mater Sci Mater Med 2006, 17: 583-596.
Yuan, et al., "Osteoinduction by calciumphosphate biomaterials", Journal of Materials Science: Materials in Medicine 9 (1998) 723-726.
Napper et al., Characterisation, quantity and sorptive properties of microplastics extracted from cosmetics, Marine Pollution Bulletin, vol. 99, Issues 1-2, Oct. 15, 2015, pp. 178-185.
International Preliminary Report on Patentability of the International Searching Authority; PCT/US2017/034405; Mailed Dec. 6, 2018; 9 pages; European Patent Office.
International Preliminary Report on Patentability of the International Searching Authority; PCT/US2017/034409; Mailed Dec. 6, 2018; 12 pages; European Patent Office.
International Preliminary Report on Patentability of the International Searching Authority; PCT/US2017/034417; Mailed Dec. 6, 2018; 13 pages; European Patent Office.
International Preliminary Report on Patentability of the International Searching Authority; PCT/US2017/034421; Mailed Dec. 6, 2018; 9 pages; European Patent Office.
International Preliminary Report on Patentability of the International Searching Authority; PCT/US2018/062673; Mailed Jun. 11, 2020; 9 pages; European Patent Office.
International Preliminary Report on Patentability of the International Searching Authority; PCT/US2018/062675; Mailed Jun. 11, 2020; 11 pages; European Patent Office.
International Search Report and Written Opinion of the International Searching Authority; PCT/US17/034405; Mailed Jul. 21, 2017; 11 pages; European Patent Office.
International Search Report and Written Opinion of the International Searching Authority; PCT/US17/034409; Mailed Oct. 4, 2017; 16 pages; European Patent Office.
International Search Report and Written Opinion of the International Searching Authority; PCT/US17/034417; Mailed Jan. 9, 2018; 17 pages; European Patent Office.
International Search Report and Written Opinion of the International Searching Authority; PCT/US17/034421; Mailed Jul. 20, 2017; 12 pages; European Patent Office.
International Search Report and Written Opinion of the International Searching Authority; PCT/US18/062675; Mailed Apr. 8, 2019; 14 pages; European Patent Office.
International Search Report and Written Opinion of the International Searching Authority; PCT/US2018/062671; Mailed Apr. 29, 2019; 15 pages; European Patent Office.
International Search Report and Written Opinion of the International Searching Authority; PCT/US2018/062673; Mailed Jan. 25, 2019; 13 pages; European Patent Office.
International Search Report and Written Opinion of the International Searching Authority; PCT/US2018/062713; Mailed May 8, 2019; 17 pages; European Patent Office.
Jacoby; "New Applications for Glass Emerge," Chem. Eng. News, 90 [25] 34-36 (2012).
Japanese Patent Application No. 2018561573 Office Action dated Feb. 24, 2021, 14 pages (7 pages of English Translation and 7 pages of Original Document); Japanese Patent Office.
Lu et al., "The Biodegradation Mechanism of Calcium Phosphate Biomaterials in Bone, Journal of Biomedical Materials Research", Aug. 2002, 63(4): 408-412.
Knowles, "Phosphate based glasses for biomedical applications", J. Mater. Chem., 2003, 13, 2395-2401.
Jones; "Review of Bioactive Glass: From Hench to Hybrids"; Acta Biomaterialia 9 (2013) pp. 4457-4486.
Kaklamani et al., "Mechanical Properties of Alginate Hydrogels Manufactured Using External Gelation", J. Mech Beh. Biomed. Mater., 2014, pp. 135-142 (Year: 2014).
Noris-Suarez et al., "Osteoblastic cells biomineralized on bioactive glass and glass-ceramics of the Si02. Na20.CaO.K 20.Mg O.P205 system modified with Al203 and B203", Journal of Ceramic Processing Research, vol. 11, No. 2, 2020, 9 pages.
Kokubo et al., "How Useful is SBF in Predicting in vivo Bone Bioactivity?"; Biomaterials, 27, (2006), 2907-2915.
Kumaryadav et al., "Development of Zirconia Substituted 1393 Bioactive Glass for Orthopaedic Application"; Oriental Journal of Chemistry; vol. 33, No. 6; (2017) pp. 2720-2730.
Hench et al., "Third-Generation Biomedical Materials", Science, vol. 295, Feb. 8, 2002, p. 1016-1017, www.sciencemag.org, Downloaded from www.sciencemag.org on Aug. 5, 2015.
L. Hench, and J. Jones, eds. Biomaterials, artificial organs and tissue engineering. Elsevier, 2005—book.
Lien et al., "Microstructural Evolution and Physical Behavior of a Lithium Disilicate Glass-Ceramic"; Dent Mater 2015, 31: 928-940.
Liu et al., "The Effect of Novel Fluorapatite Surfaces on Osteoblast-Like Cell Adhesion, Growth, and Mineralization" Tissue Engineering: Part A, vol. 16, No. 9, 2010 (Year: 2010).
Low et al., "Reduction in Dental Hypersensitivity with Nano-Hydroxy Apatite, Potassium Nitrate, Sodium Monoflurophosphate and Antioxidants"; The Open Dentistry Journal; (2015), 9, pp. 92-97.
Maestrelli et al., "Development of Enteric-Coated Calcium Pectinate Microspheres Intended for Colonic Drug Delivery", Eur. J. Pharm. and Biopharm., 2008, pp. 508-518 (Year: 2008).
Marcolongo et al., "Surface Reaction Layer Formation in vitro on a Bioactive Glass Fiber/Polymeric Composite"; J. Biomed Mater. Res.; (1997); 37, pp. 440-448.

(56) References Cited

OTHER PUBLICATIONS

Montazerian et al., "History and trends of bioactive glass-ceramics", Journal of Biomedical Materials Research A, 2016, vol. 104A, 1231-1249, 2016 Wiley Periodicals, Inc.
Miglani et al., "Dentin Hypersensitivity: Recent Trends in Management" ; J. Conserv. Dent. 2010; 13 (4) pp. 218-224.
Mintatoya et al., "Bioactive Glass Cloth That Propmotes New Bone Formation"; Key Eng. Mater.; (2013) 529-530; pp. 266-269.
Rahaman et al., "Bioactive glass in tissue engineering", Acta Biomaterialia vol. 7, issue 6, pp. 2355-2373.
Morch et al., "Effect of Ca2+, Ba2+, and Sr2+ on Alginate Microbeads"; Biomacromolecules 2006, 7, 1471-1480.
Uo et al., "Properties and cytotoxicity of water soluble Na2O-CaO-P2O5 glasses", Biomaterials, 19, (1998), 2277-2284.
Neel et al., "Characterisation of Antibacterial Copper Releasing Degradable Phosphate Glass Fibres." Biomaterials 26, No. 15 (2005): 2247-2254.
Ning et al. "Effects of silica on the bioactivity of calcium phosphate composites in vitro" Journal of Materials Science: Materials in Medicine 16 (2005) 355-360 (Year: 2005).
Ning et al., "Food Biochemistry" South China University of Technology Press, Edition 1, 1995, 9 pages (5 pages of English Translation and 14 pages of Original Document).
Ogonczyk et al., "Microfluidic formulation of pectin microbeads for encapsulation and controlled release of nanoparticles," Biomicrofluidics, 2011, pp. 1-12.
Ohgushi et al., "AI2O3 doped apatite-wollastonite containing glass ceramic provokes osteogenic differentiation of marrow stromal stem cells", J Biomed Mater Re, vol. 44, Issue 4 pp. 381-388.
Ohgushi et al., Bioceramics vol. 11, Legeros et al, Ed., Proc. 11th Int. Symp. Ceramics. Med. (NY:NY), Nov. 1998, pp. 261-264 (Year 1998).
Peddi et al., "Bioactive Borate Glass Coatings for Titanium Alloys", J. Mater. Sci: Mater. Med., (2008), 19, p. 3145-3152.
Pires et al., "The Role of Alumina in Aluminoborosilicate Glasses for Use in Glass-Ionomer Cements"; J. Mater. Chem, 19 (2009) pp. 3652-3660.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Sglavo; "Chemical Strengthening of Soda Lime Silicate Float Glass: Effect of Small Differences in the KNO3 Bath," Int J Appl Glass Sci, 2015, 6: 72-82.
Sharmikn et al., "Effect of Boron Additiona on the Thermal, Degradation, and Cytocompatibility Properties of Phosphate-Based Glasses"; Biomed Research Internaitonal; vol. 2013; Article ID 902427; 12 pages.
Simhan; "Chemical Durability of ZrO2 Containing Glasses"; Journal of Non-Crystalline Solids; 54 (1983) 335-343.
Singh et al., "Characterization of SI02-NA20-FE2O3-CAO-P2O5 B2O3 Glass Ceramics"; Journal of Materials Science: Materials in Medicine, 10(8) pp. 481-484. (1999).
Strassler et al., "Dentinal Hypersensitivity: Etiology, Diagnosis and Management"; 9 Pages; Date Unknown; www.indeedce.com.
Succaria et al., "Prescribing a Dental Ceramic Material: Zirconia vs Lithium-Disilicate"; The Saudi Dent J, 2011, 23: 165-166.
Taiwanese Patent Application No. 107142436, Office Action, dated Jun. 2, 2022, 1 page; Taiwanese Patent Office.
Budov "Hollow glass microspheres. Use, properties and technology (review article)", Glass Ceram, 1994, 51: 230-235.
Wallenberger et al., "The Liquidus Temperature; Its Critical Role in Glass Manufacturing"; International Journal of Applied Glass Science 1 [2] (2010) pp. 151-163.
Wang Yingjun, "Biomedical Ceramic Materials", Guangzhou, South China University of Science and Technology Press, , Aug. 31, 2010, pp. 90-93(Original document only).

Xiao et al., "Hollow Hydroxyapatite Microspheres: A Novel Bioactive and Osteoconductive Carrier for Controlled Release of Bone Morphogenetic Protein-2 in Bone Regeneration", Acta Biomater. Sep. 2013; 9(9): 8374-8383.
Yao et al., "In Virto Bioactive Characteristics of Borate-Based Glasses with Controllable Degradation Behavior"; J. Am. Ceram. Soc.; 90 [1]; 303-306 (2007).
Yin et al., "Effect of Zr02 on the Bioactivity Properties of Gel-Derived Ca0-P205-Si02-Sr0 Glasses"; Ceramics International; 43 (2017) pp. 9691-9698.
Yue et al., "Fiber Spinnability of Glass Melts"; International Journal of Applied Glass Science; (2016) pp. 1-11.
Zahid et al., "Biological Behavior of Bioactive Glasses and their Composites"; RSC Adv., 2016, 5 pp. 70197-70214.
Zhang et al., "Chipping Resistance of Graded Zirconia Ceramics for Dental Crowns"; J Dent Res, 2012, 91:311-315.
Zhao et al., "Mechanism for converting AI2O3-containing borate glass to hydroxyapatite in aqueous phosphate solution", In Acta Biomaterialia, No. 4, vol. 5, 2009, Part 3.1 of p. 1268, list 1, Fig. 2 abstract.
Zheng et al., "Characteristics and Biocompatibility of Na20-K20-Ca0-Mg0-Sr0-B2O3-P205 Borophosphate Glass Fibers"; Journal of Non-Crystalline Solids; 358 (2012) 387-391.
Saranti et al., "Bioactive glasses in the system CaO—B2O3—P2O5; preparation, structural study and in vitro evaluation"; Journal of Non-Crystalline Solids 352, No. 5 (2006): 390-398.
Abo-Naf et al., "In Vitro Bioactivity Evaluation, Mechanical Properties and Microstructural Characterization of Na2O—CaO—B2O3—P2O5 Glasses"; Spectrochimica Acta Part A: Molecular and Biomolecular Spectroscopy; 144 (2015) pp. 88-98.
Ahmed et al., "Processing, Characterisation and Biocompatibility of Iron-Phosphate Glass Fibres for Tissue Engineering", Biomaterials, 25, (2004), 3223-3232.
American Type Culture Collection, Product Sheet MC3T3E1, Subclone 14, (ATCC.RTM. CRL2594.TM.), p. 1-3, Aug. 2014.
Kulal et al., "An In-Vitro Comparison of Nano Hydroxyapatite, Novamin and Proargin Desensitizing Toothpastes—A SEM Study;" J Clin Diagn Res, 2016, 10(10): ZC51ZC54.
Andersson et al., "In vivo behaviour of glasses in the Si02-Na20-Ca0-P205-AI2O3-B2O3 system", J. Mat. Sci: Materials in Medicine (1990) 1: pp. 219-227.
Tilocca et al., "Structural Effects of Phosphorus Inclusion in Bioactive Silicate Glasses", J. Phys. Chem. B., 2007, 111, 14256-14264.
Apel et al., "Influence of Zr02 on the crystallization and properties of lithium disilicate glass-ceramics derived from a multi-component system", J. Eur. Ceram. Soc., 2007, 27:1571-1577.
Azo Materials, "Silicon Dioxide", accessed from: ""https://www.azom.com/properties.aspx?ArticleI D=1114"", accessed on Feb. 19, 2019,pp. 1-4 (Year. 2019).
Bunker et al., "Phosphate Glass Dissolution in Aqueous Solutions", Journal of Non-Crystalline Solids 64 (1984) 291-316.
Bertling et al., "Hollow Microspheres". Chem Eng Technol, 2004, 27: 829-837.
Brown et al., "Effect of Borate Glass Composition on its Conversion to Hydroxyapatite and on the Proliferation of MC3T3-E1 Cells"; Journal of Biomedical Materials Research Part A 88, No. 2, (2009): 392-400.
Buchilin et al., "Crystallization-Controlled Pore Retention in Calcium-Phosphate Glassceramics from Powder Sintering of Ca0-P205-B2O3-AI2O3-Ti02-Zr02 Glass"; Journal of Non-Crystalline Solids; 373-374 (2013) pp. 42-50.
Rochman et al., "Scientific evidence supports a ban on microbeads", Environ Sci & Tech, 2015, 49: 10759-10761.
Cao et al., "Bioactive Materials"; Ceramics International, 22, (1996) 493-507.
Cao et al., "Methods for Biomimetic Remineralization of Human Dentine: A Systematic Review"; Int. J. Mol. Sci. (2015) 16; pp. 4615-4627.
Chinese Patent Application No. 201780033194.7, Office Action dated May 6, 2021, 5 pages (English Translation Only), Chinese Patent Office.

(56) References Cited

OTHER PUBLICATIONS

Chinese Patent Application No. 201880075910.2, Office Action dated Sep. 16, 2021, 10 pages (6 pages of English Translation and 4 pages of Original Document), Chinese Patent Office.
Chinese Patent Application No. 201780032795.6, Office Action dated Apr. 19, 2021; 15 pages (English Translation only); Chinese Patent Office.
Chinese Patent Application No. 201780032815, Office Action dated Jun. 1, 2021, 7 pages (English Translation Only); Chinese Patent Office.
Chinese Patent Application No. 201780032822.X, Office Action dated Dec. 10, 2021, 22 pages (12 pages of English Translation and 10 pages of Original Copy), Chinese Patent Office.
Chinese Patent Application No. 201780032822.X, Office Action dated May 26, 2021; 5 pages (English Translation Only); Chinese Patent Office.
Chinese Patent Application No. 201780032836.1, Office Action dated Jun. 15, 2021, 11 pages (5 pages of English Translation and 6 pages of Original Document), Chinese Patent Office.
Chinese Patent Application No. 201780032893, Office Action dated May 17, 2021; 14 pages (English Translation only); Chinese Patent Office.
Chinese Patent Application No. 201780032893.X, Office Action dated Nov. 17, 2021, 4 pages English Translation, Chinese Patent Office.
Chinese Patent Application No. 201780033194.7, Office Action dated Nov. 24, 2021, 4 pages of English Translation, Chinese Patent Office.
Chinese Patent Application No. 201880077025.8, Office Action dated Feb. 28, 2022, 09 pages of English Translation, Chinese Patent Office.
Chinese Patent Application No. 201880077026.2, Office Action dated Mar. 19, 2022, 5 pages of English Translation, Chinese Patent Office.
Chinese Patent Application No. 201880077082.6, Office Action dated Mar. 1, 2022, 10 pages of English Translation, Chinese Patent Office.
Copeland et al., "Microbeads: An Emerging Water Quality Issue", Retrieved from fas.org, Jul. 20, 2015, 2 pgs.
Coradin et al., "Silica-Alginate Composites for Microencapsulation" Applied Microbiology and Biotechnology, 61(5-6) pp. 429-434 (2003).
Davari, "Dentin Hypersensitivity: Etiology, Diagnosis and Treatment, a Literature Review," J Dent (Shiraz), 2013, 14(3): 136-145.
De Kerchove et al., "Formation of Polysaccharide Gel Layers in the Presence of Ca2+ and K+ Ions: Measurements and Mechanisms", Biomacromolecules 2007, 8, 113-121.
Zanotto, "A bright future for glass-ceramics", American Ceramic Society Bulletin, vol. 89, No. 8, pp. 19-27, 2010.
Abou Neel et al., "Effect of iron on the surface, degradation and ion release properties of phosphate-based glass fibres." Acta Biomaterialia 1, No. 5 (2005): 553-563.
El-Kheshen et al., "Effect of Al2O3 Addition on Bioactivity, Thermal and Mechanical Properties of Some Bioactive Glasses"; Ceramics Int. (2008) 34: 1667-1673 (Year: 2008).
European Patent Application No. 17728378.5 Office Action dated Jun. 21, 2021; 6 Pages; European Patent Office.
European Patent Application No. 17729964.1 Office Action dated Dec. 2, 2020; 4 Pages; European Patent Office.
European Patent Application No. 17729964.1 Office Action dated Dec. 18, 2019; 6 Pages; European Patent Office.
F. Jay Murray, "Issues in Boron Risk Assessment: Pivotal Study, Uncertainty Factors, and ADIs", The Journal of Trace Elements in Experimental Medicine 9, No. 4 (1996): 231-243.
Fabienne C. Raszewski et al., "Methods For Producing Hollow Glass Microspheres", Savannah River National Laboratory, Aiken, SC 29808, Mar. 2016.
Fendall et al., "Contributing to Marine Pollution by Washing Your Face: Microplasitcs in Facial Cleansers"; Marine Pollution Bulletin 58 (8): 1225-1228 (2009)).
Forsback et al., "Mineralization of Dentin Induced by Treatment with Bioactive Glass S53P4 in Vitro"; ACTA Odontol Scand, 62 (2004); pp. 14-20.
Franks et al., "The Effect of MgO on the Solubility Behaviour and Cell Proliferation in a Quaternary Soluble Phosphate Based Glass System", J. of Mate. Science: Materials in Medicine, 13, (2002), 549-556.
Fu et al., "Bioactive Glass Innovations Through Academia-Industry Collaboration"; International Journal of Applied Glass Science, 7 [2], (2016) pp. 139-146.
Fu et al., "Nature-Inspired Design of Strong, Tough Glass-Ceramics," MRS Bulletin, 2017, 42:220-225.
Fu et al., "Silicate, Borosilicate, and Borate Bioactive Glass Scaffolds With Controllable Degradation Rate for Bone Tissue Engineering Applications. I. Preparation and in Vitro Degradation"; Journal of Biomedical Materials Research A; 2010; vol. 95A; Issue 1; pp. 164-171.
Fu et al., "Hollow hydroxyapatite microspheres as a device for controlled delivery of proteins"; J Mater Sci: Mater Med., 2011, 22: 579-91.
Fuat Topuz et al., "Magnesium ions and alginate do form hydrogels: a rheological study", Soft Matter, Aug. 2012, 4877-4881.
Mohini et al., "Studies on influence of aluminium ions on the bioactivity of B2O3-SiO2-P2O5-Na2O-CaO glass system by means of spectroscopic", Applied Surface Science, vol. 287, 2013, pp. 46-53.

* cited by examiner

HIGH LIQUIDUS VISCOSITY BIOACTIVE GLASS

CROSS-REFERENCE TO RELATED APPLICATIONS

This application is a divisional of U.S. application Ser. No. 16/202,952 filed on Nov. 28, 2018, which claims the benefit of priority under 35 U.S.C. § 119 of U.S. Provisional Patent Application No. 62/591,446 filed Nov. 28, 2017, the content of which is incorporated herein by reference in its entirety.

The present application is related commonly owned and assigned USSN Provisional Application Nos., filed May 25, 2016:

62/342,384, entitled "BIOACTIVE ALUMINOBORATE GLASSES";
62/342,377, entitled "MAGNETIZABLE GLASS CERAMIC COMPOSITION AND METHODS THEREOF";
62/342,381, entitled "LITHIUM DISILICATE GLASS-CERAMIC COMPOSITIONS AND METHODS THEREOF";
62/342,391, entitled "BIODEGRADABLE MICRO-BEADS"; and
62/342,411, entitled "BIOACTIVE GLASS MICRO-SPHERES"; but does not claim priority thereto.

The present application is also related commonly owned and assigned USSN Application Nos.:

62/591,423 filed Nov. 28, 2017, entitled "BIOACTIVE GLASS COMPOSITIONS AND METHODS OF TREATING DENTIN HYPERSENSITIVITY";
62/591,438, filed Nov. 28, 2017, entitled "CHEMICALLY STRENGTHENED BIOACTIVE GLASS-CERAMICS"; and
62/591,429, filed Nov. 28, 2017, entitled "BIOACTIVE BORATE GLASS AND METHODS THEREOF", filed concurrently herewith, but does not claim priority thereto.

The entire disclosure of each publication or patent document mentioned herein is incorporated by reference.

BACKGROUND

The disclosure relates to a bioactive glass having a high liquidus viscosity, and to methods of making and using the bioactive glass.

SUMMARY

In embodiments, the present disclosure provides bioactive glass compositions. The bioactive glass compositions can comprise, for example, in weight percentage (wt %), 50 to 70% $SiO_2$, 0.1 to 10% $Al_2O_3$, 5 to 30% $Na_2O$, 0.1 to 15% $K_2O$, 0.1 to 15% MgO, 0.1 to 20% CaO, and 5 to 10% $P_2O_5$, based on 100 wt % total.

In embodiments, the disclosure provides bioactive glass compositions having components, for example, in weight percentage, of from 60 to 70% $SiO_2$, of from 15 to 30% $Na_2O$, of from 5 to 15% $K_2O$, of from 1 to 10% CaO, and of from 5 to 10% $P_2O_5$, i.e., free of $Al_2O_3$, MgO, or both.

In embodiments, the present disclosure provides bioactive glass compositions having a relatively high viscosity, which viscosity enables different or alternative forming methods.

In embodiments, the present disclosure provides bioactive glass compositions having excellent biocompatibility.

In embodiments, the present disclosure provides bioactive glass compositions that can be continuously drawn into glass fibers having a diameter, for example, of from 1 to 100 microns.

BRIEF DESCRIPTION OF THE DRAWINGS

In embodiments of the disclosure.

DETAILED DESCRIPTION

Figure 1:
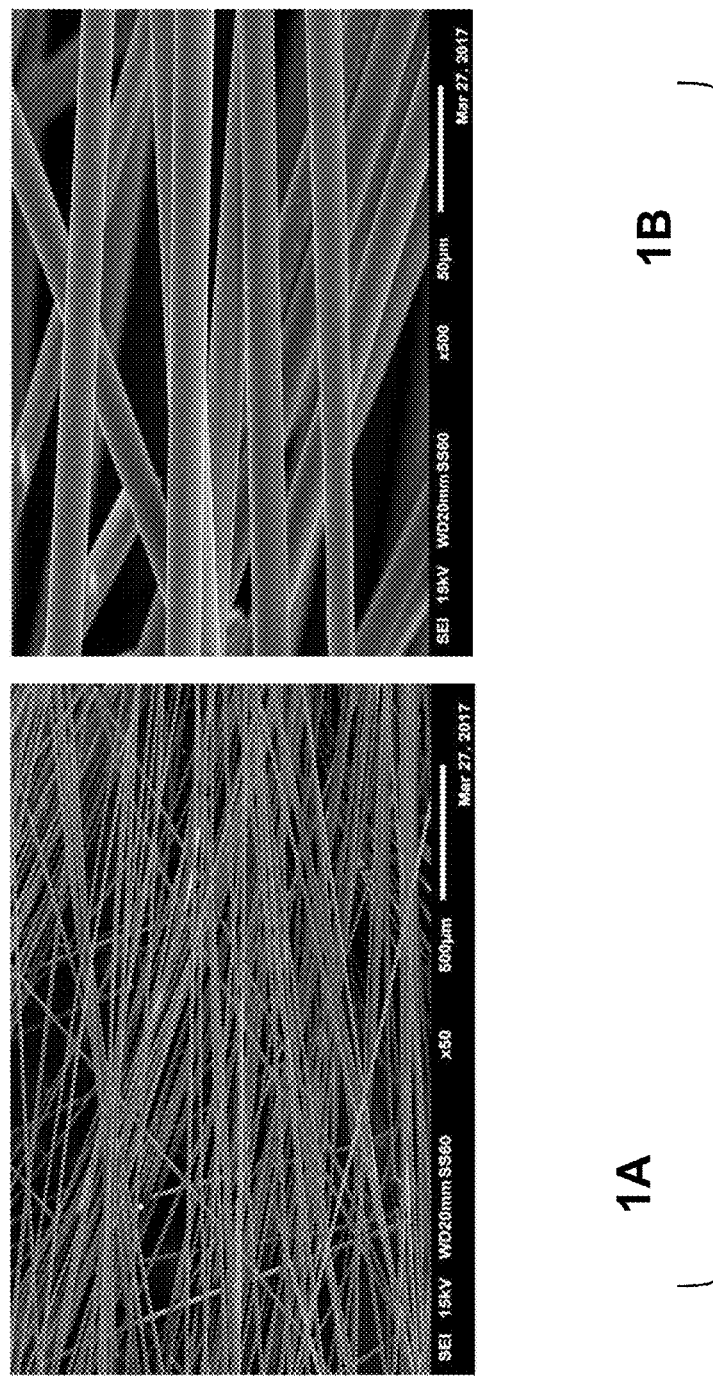
FIGS. 1A and 1B show SEM images at 500 micron (1A) and 50 microns (1B) scales, respectively, of glass fibers produced using a down-draw process from disclosed Composition 5 in Table 1.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, and methods of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Liquidus temperature" ($T_L$ or $T_{liq}$) refers to the boundary temperature at which a first crystalline compound is formed when the glass specimen is held at a specific temperature gradient over the gradient's entire length for a period of time necessary to obtain a thermal equilibrium between the crystalline and glassy phases (see ASTM C829-81). A liquidus temperature of a glass can be measured using the gradient furnace method specified by ASTM C829-81.

"High temperature viscosity" refers to (no the measure of the resistance of a liquid to gradual deformation by shear stress or tensile stress. The viscosity of glass above its softening point can be measured using a platinum alloy spindle immersed in a crucible of molten glass as specified by ASTM 965-96. Liquidus viscosity refers to the glass viscosity at the corresponding liquidus temperature.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "hr" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

In embodiments, the disclosure relates to a bioactive glass having an ability to bond strongly with hard and soft mammalian tissue, and to foster the growth of bone and cartilage cells (see Rahaman, et al., Bioactive glass in tissue engineering, Acta Biomater 2011, 7: 2355-2373). Bioactive glasses have been reported to release ions that activate expression of osteogenic genes, and stimulate angiogenesis (see Rahaman, supra.). Example commercial products including, for example, Perioglas® (NovaBone Products LLC, Alachua, FL), Novabone® (NovaBone Products LLC), or NovaMin® (Glaxo-Smith-Kline, UK) are based on bioactive glass particles (see Jones, Review of bioactive glass: From Hench to hybrids. Acta Biomater 2013, 9: 4457-4486). The low liquidus viscosity of traditional bioactive glasses limited their forming capability (see Q. Fu, et al., Bioactive Glass Innovations Through Academia-Industry Collaboration. Int J Appl Glass Sci, 2016, 7: 139-146). For example, the benchmark bioactive glass 45S5 composition has a liquidus viscosity of 24 poise at 1185° C. (Control 1 herein in Table 1) while another well-studied glass 13-93 glass composition has a liquidus of 200 poise at 1145° C. (Control 2 herein in Table 1). In comparison, traditional soda lime silicate glass has a liquidus viscosity of about 10,000 poise at 1010° C. (see Q. Fu, et al., supra.; and Wallenberger, et al., The Liquidus Temperatures; Its Critical Role in Glass Manufacturing, Int J Appl Glass Sci, 2010, 1:151-163).

In embodiments, the disclosure provides a bioactive glass composition comprising:
50 to 70% $SiO_2$;
0.1 to 10% $Al_2O_3$,
5 to 30% $Na_2O$,
0.1 to 15% $K_2O$,
0.1 to 15% MgO,
0.1 to 20% CaO, and
5 to 10% $P_2O_5$, based on a 100 wt % of the composition.

In embodiments, the liquidus viscosity of the composition can be, for example, of from 200 to 5,000 poise.

In embodiments, the bioactive glass composition can have, for example, a biocompatibility of at least one of, for example, a proliferation of a live cell line on the surface of the bioactive glass, a continuous cell number increase of from 0 to 7 days, or a combination thereof.

In embodiments, the composition as a drawn fiber form factor can have a diameter of from 1 to 100 microns.

In embodiments, the disclosure can provide, for example, a dental formulation, a wound healing formulation, a bone growth or restoration formulation, and like useful formulations.

In embodiments, the composition can further comprise formulation ingredients, for example, a carrier in an amount of from 5 to 300 wt % by superaddition to the bioactive glass composition to form a bioactive glass formulation. The carrier can be, for example, any known solid, liquid, gel, or a combination thereof. Formulation of the bioactive glass composition with a carrier can provide many advantages, such as pre-selected dose levels, pre-selected concentrations, stabilized mixtures or suspensions of the bioactive glass and an adjuvant, and like advantages.

In embodiments, the carrier can be, for example, one or more ingredients selected from: an abrasive, a humectant, i.e., an anti-drying agent such as glycerol, sorbitol, xylitol, 1,2-propylene glycol, polyethyleneglycol, and like compounds, a flavorant, a colorant, an antibacterial agent, a surfactant, a whitening agent, and other like suitable ingredients known in the art, or a mixture thereof.

In embodiments, the disclosure provides a dental formulation composition wherein the suitable carrier comprises one or more forms selected from: a gum, a paste, a powder, a toothpaste, a mouthwash, a poultice, a tea, a sucker, a spray, and like forms, or a mixture thereof.

In embodiments, the disclosure provides a preferred bioactive glass composition comprising:
60 to 70% $SiO_2$,
15 to 30% $Na_2O$,
5 to 15% $K_2O$,
1 to 10% CaO, and
5 to 10% $P_2O_5$, based on a 100 wt % of the composition.

In embodiments, the preferred bioactive glass composition can be free of $Al_2O_3$, MgO, or both.

In embodiments, the preferred bioactive glass composition can further comprise, for example, a carrier in an amount of from 5 to 300 wt % by superaddition to the bioactive glass composition to form a bioactive glass formulation as mentioned above.

In embodiments, the disclosure provides a method of making a bioactive glass fiber comprising, for example:
forming a melt of the glass composition comprising:
50 to 70% $SiO_2$;
0.1 to 10% $Al_2O_3$,
5 to 30% $Na_2O$,
0.1 to 15% $K_2O$,
0.1 to 15% MgO,
0.1 to 20% CaO, and
5 to 10% $P_2O_5$, based on a 100 wt % of the composition,
until the melt has a viscosity of from 200 to 2,000 poise; and drawing the melt into a fiber.

In embodiments, the drawn glass fiber can have, for example, a diameter of from 1 to 100 microns.

In embodiments, drawing the melt into a fiber can be accomplished, for example, batch-wise, semi-continuously, or continuously.

In embodiments, the temperature of the glass in the melt can be, for example, from 1050 to 1,200° C., and is above the glass liquidus temperature by from 10 to 200° C.

The present disclosure is advantaged is several aspects, including for example:

The disclosed bioactive glass compositions have much higher liquidus viscosities such as at least ten times higher compared to a benchmark 45S5 bioactive glass, which makes the disclosed bioactive glass compositions more suitable for an industrial manufacturing platform.

The disclosed bioactive glass compositions have excellent biocompatibility as demonstrated by, for example, in vitro cell culture studies. These studies demonstrated the desired capability to support cell attachment and growth over a period of up to 7 days.

The disclosed bioactive glass compositions can be continuously drawn into glass fibers having a diameter of from 1 to 100 microns from a glass melt.

In embodiments, the present disclosure provides bioactive glass compositions that have demonstrated high liquidus viscosity and excellent biocompatibility. The improved liquidus of the disclosed compositions permits, for example, glass fibers of from 1 to 100 microns to be continuously drawn.

In embodiments, the disclosed glass, for example, in a batch composition or a finished glass, comprises, for example, in weight percentage, of from 50 to 70% $SiO_2$, of from 0.1 to 10% $Al_2O_3$, of from 5 to 30% $Na_2O$, of from 0.1 to 15% $K_2O$, of from 0.1 to 15% MgO, of from 0.1 to 20% CaO, and of from 5 to 10% $P_2O_5$. Example compositions are listed in Table 1.

In embodiments, a more preferred composition can be, for example, in weight percentage, of from 60 to 70% $SiO_2$, of from 15 to 30% $Na_2O$, of from 5 to 15% $K_2O$, of from 1 to 10% CaO, and of from 5 to 10% $P_2O_5$. These glasses can typically be melted at a temperature below 1300° C., and in certain embodiments below 1400° C., making it possible to make melts in a relatively small commercial glass tank.

Table 1 lists exemplary as-batched compositions 1 to 8, and control 1 (45S5) and control 2 (13-93).

TABLE 1

As-batched compositions.

| Composition > Oxides (wt %) | Contro 11 | Contro 12 | 1 | 2 | 3 | 4 | 5 | 6 | 7 | 8 |
|---|---|---|---|---|---|---|---|---|---|---|
| $SiO_2$ | 45 | 53 | 65.6 | 64.4 | 64.4 | 63.2 | 62.1 | 64.4 | 63.2 | 61.0 |
| $Na_2O$ | 24.5 | 6 | 22.5 | 22.1 | 22.1 | 21.7 | 21.3 | 22.1 | 21.7 | 20.9 |
| K2O | 0 | 12 | 0.0 | 0.0 | 1.8 | 3.6 | 5.3 | 0.0 | 0.0 | 3.4 |
| CaO | 24.5 | 20 | 4.6 | 4.5 | 4.5 | 4.4 | 4.3 | 4.5 | 4.4 | 4.3 |
| MgO | 0 | 5 | 0 | 0 | 0 | 0 | 0 | 1.8 | 3.6 | 3.4 |
| $P_2O_5$ | 6.0 | 4 | 7.4 | 9.1 | 7.3 | 7.1 | 7.0 | 7.3 | 7.1 | 6.9 |
| $T_{liq}$ (° C.) | 1185 | 1145 | 1105 | 1195 | 1005 | 1015 | 990 | 1070 | 1090 | 1040 |
| $\eta_{liq}$ (poise) | 24 | 200 | 765 | 335 | 657 | 1679 | 2000 | 1131 | 883 | 1230 |

The liquidus viscosity ($\eta_{liq}$) of presently disclosed compositions can be, for example, up to 2,000 poise (Table 1), which makes them compatible with a wide range of forming methods including pressing, blowing, casting, thin rolling, floating, and like methods. This formability enables different forming factors from the disclosed compositions. These glasses can be processed by different techniques into, for example, powder, fibers, beads, sheets, or 3-D scaffolds. A glass powder can generally be prepared by, for example, jet milling or ball milling of glass frits; short fibers can be made by, for example, melt spinning or electric spinning; beads can be produced by, for example, flowing glass particles through a vertical furnace; sheets can be made by, for example, using thin rolling, floating or fusion-draw processes; and scaffolds can be produced by, for example, using rapid prototyping, polymer foam replication, particle sintering, and like methods. Disclosed glasses of desired forms can be used, for example, to support cell growth, soft and hard tissue regeneration, stimulation of gene expression, angiogenesis, and like applications.

Continuous fibers can be easily drawn from the claimed glass compositions. Fiber can be formed using a directly heated (i.e., electricity passing directly through) platinum bushing. Glass cullet is loaded into the bushing, and heated until the glass melts. Temperatures are set of from 1000 to 1200° C. to achieve a desired glass viscosity of, for example, from 200 to 2000 poise, from 335 to 2000 poise, from 200 to 1500 poise, for example, less than 1,000 poise, allowing a drip to form on the orifice in the bushing. The bushing size can be selected to create a restriction that influences possible fiber diameter ranges. The drip can be manually pulled to begin forming a fiber. Once a fiber is established the fiber can be connected to a rotating pulling and collection drum to continue the pulling process at a consistent speed. Using the drum speed (or revolutions per minute RPM) and glass viscosity, the fiber diameter can be manipulated, i.e., varied and controlled. Generally, the faster the fiber pull speed, the smaller the fiber diameter. It is significant to keep the glass temperature above the glass liquidus temperature so that devitrification is eliminated (or reduced) on the bushing orifice (see Yue, et al., Fiber Spinnability of Glass Melts, *Int. J. Appl. Glass Sci.* 2017, 8: 37-347). When devitrification (i.e., crystallization) begins to form, the fiber will tend to break due to the slow glass flow or the loss of glass flow completely. Glass fibers having diameters of from 1 to 100 microns can be drawn continuously from a glass melt (see FIGS. 1A and 1B). Alternatively, test fibers can also be created using an updraw process. In this process, fibers are pulled from a glass melt surface sitting in a box furnace. By controlling the viscosity of the glass, a quartz rod is used to pull glass from the melt surface to form a fiber. The fiber can be continuously pulled upward to increase the fiber length. The pull up velocity of the rod determines the fiber thickness.

Figure 2:
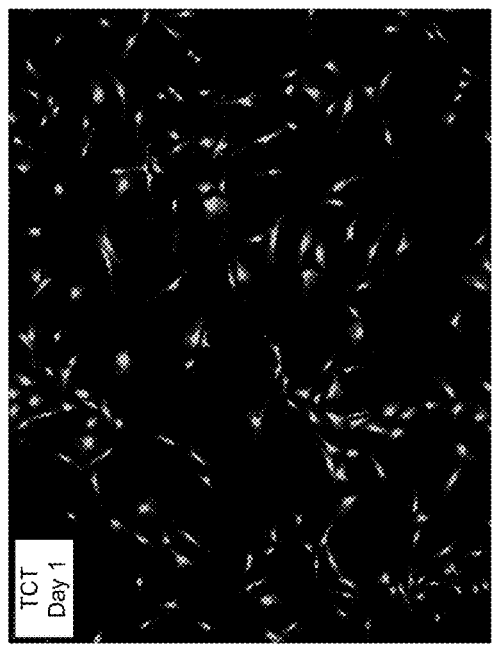
FIGS. 2A to 2D show optical images of cell morphology from live/dead cells assay.
Figure 2:
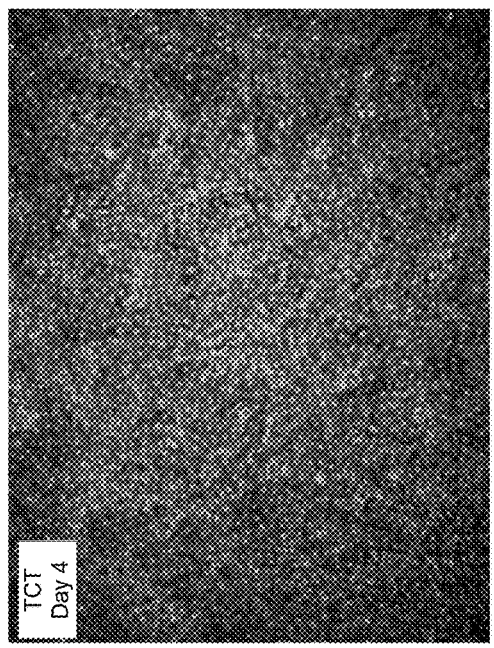
Figure 2:
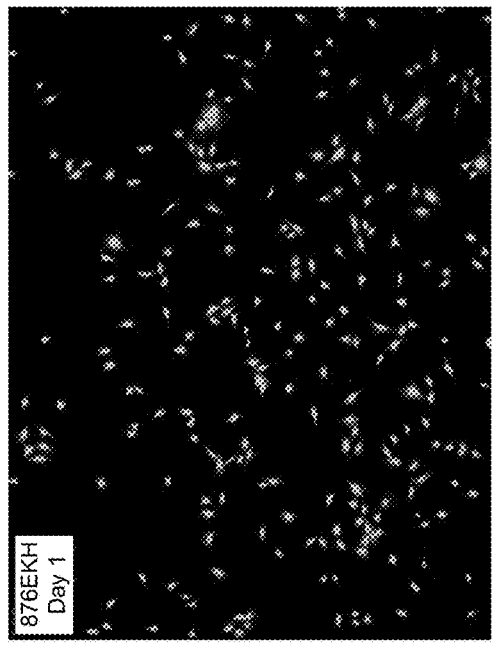
Figure 2:
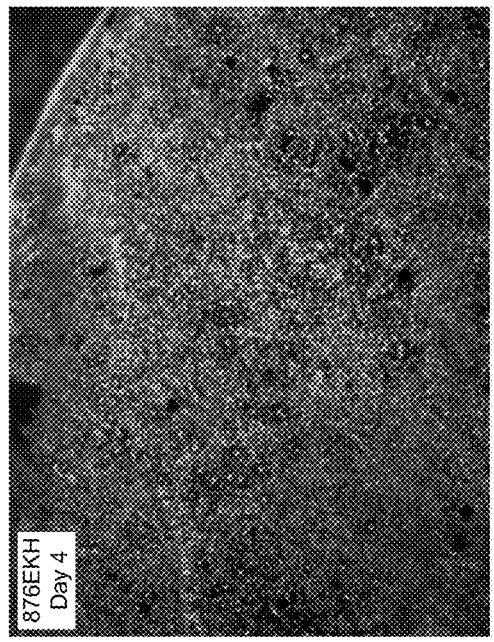

Excellent biocompatibility was demonstrated in each of the example glass Compositions 1 to 8 in Table 1. Cell attachment and growth were clearly observed on the surfaces of example glass articles made from the disclosed compositions, and in the TCT culture wells. No visible difference in cell morphology was observed between the disclosed compositions and the TCT culture wells. FIGS. 2A to 2D show optical images of cell morphology from live/dead cells assay. A cell culture using MC3T3 cell line was accomplished on glass discs (12.5 mm in diameter×2.0 mm thick) of Composition 5 in a 24-well culture plate. Spots (green in original; not provided) represent the viable cells, and spots (red in original; not provided) represent dead cells. No dead cells (i.e., red images) were visible in any of the FIG. 2 images. FIG. 2A shows the cell culture at day 1 and FIG. 2B shows the cell culture at day 4. For comparison, images of cells cultured in tissue culture-treated (TCT) wells were obtained and shown in FIGS. 2C and 2D (for days 1 and 4 respectively).

The biocompatibility and degradation can be influenced by the composition of the glass. In the disclosed glass compositions, $SiO_2$ can serve as the primary glass-forming oxide. However, the glasses preferably do not contain too much $SiO_2$ since the melting temperature (e.g., 200 poise temperature) of pure $SiO_2$ or high-$SiO_2$ glasses is too high. Furthermore, the bioactivity of glass will be decreased with high $SiO_2$ content (see L. L. Hench, Bioceramics, J Am Ceram Soc, 1998, 81:1705-1728).

$P_2O_5$ can also serves as a network former. Furthermore, the liberation of phosphate ions to the surface of bioactive glasses can contribute to the formation of apatite. The provision of phosphate ions by the bioactive glass increases apatite formation rate and the binding capacity of the bone tissue. In addition, $P_2O_5$ increases the viscosity of the glass, which in turn expands the range of operating temperatures, and is advantageous to the making the glass.

Alkali oxides ($Li_2O$, $Na_2O$, $K_2O$, $Rb_2O$, and $Cs_2O$) can serve as aids in achieving low melting temperatures and low liquidus temperatures. The addition of alkali oxides has been reported to improve bioactivity (see Q. Fu, et al., *supra*.). Divalent cation oxides (such as alkaline earth oxides) can also improve the melting behavior and the bioactivity of the glass. Particularly, CaO was able to react with $P_2O_5$ to form apatite when immersed in a simulated body fluid (SBF) or in vivo. The release of $Ca^{2+}$ ions from the surface of the glass can contribute to the formation of a layer rich in calcium phosphate.

Raw materials, equipment, or both, used to produce the compositions of the present disclosure, can introduce certain impurities or components that are not intentionally added, and can be present in the final glass composition. Such materials can be present in the disclosed compositions in minor amounts and are referred to as "tramp materials."

Disclosed compositions can comprise the tramp materials, typically in trace amounts. Similarly, "iron-free," "sodium-free," "lithium-free," "zirconium-free," "alkali earth metal-free," "heavy metal-free," or like descriptions, mean that the tramp material was not purposefully added to the composition, but the composition may still comprise iron, sodium, lithium, zirconium, alkali earth metals, or heavy metals, etc., but in approximately tramp or trace amounts.

Unless otherwise specified, the concentrations of all constituents recited herein are expressed in terms of weight percent (wt %).

EXAMPLES

The following Examples demonstrate making, use, and analysis of the disclosed compositions and methods in accordance with the above general procedures.

Example 1

Bioactive Glass Melts. Glass compositions listed in Table 1 were prepared by combining the respective batch ingredients, including sand, sodium carbonate, potassium carbonate, calcium metasilicate, magnesia, di-sodium phosphate, in the indicated amounts. The batch source materials were vigorously mixed in a plastic jar using a Turbular mixer. Then they were transferred to a platinum crucible with an internal volume of approximately 650 cc. The crucible was then loaded into an annealing furnace to calcine the batch at 250° C. for 24 hr. The calcined batches were melted at from 1300 to 1500° C. for 16 hr and then the glass melt was poured on a steel plate, and annealed at from 400 to 500° C.

Example 2

Bioactive Glass Fibers. Glass compositions of Example 1 were drawn into fibers using a directly heated platinum bushing. Glass cullet was loaded into the bushing, and heated up to from 1050 to 1200° C. to obtain a glass melt. The viscosity of the melt was of from 200 to 1500 poise to allow for the formation of a glass drip on the orifice in the bushing. The drip was then pulled by hand to begin forming a fiber. Once a fiber was established the fiber was connected to a rotating pulling/collection drum to continue the pulling process at a constant speed. Using the drum speed (or revolutions per minute RPM) and glass viscosity, the fiber diameter can be manipulated. In general, the faster the pull speed the smaller the fiber diameter that results.

Example 3

Biocompatibility of Bioactive Glass Compositions. Glass discs (12.5 mm in diameter×1 mm thick) were prepared from the annealed patties of Example 1 using a diamond core drill, and then ground polished to a 1.0 micron finish using $CeO_2$ slurry. All finished parts were cleaned by sonicating in an ultrasonicater for 10 min. Then the discs were placed into wells of 24 well microplates. MC3T3 cells were seeded to each well at a density of 10K/well and cultured for 1, 4, or 7 days in a humid incubator at 37° C./5% $CO_2$. Calcein AM and ethidium homodimer-1 were used to stain live/dead cells. The cell images were captured under a fluorescent microscope and presented in FIGS. 1.

While various features, elements or steps of particular embodiments can be described using the transitional phrase "comprising," in alternative embodiments, including those that may be described using the transitional phrases "consisting" or "consisting essentially of," are possible.

The disclosure has been described with reference to various specific embodiments and techniques. However, many variations and modifications are possible while remaining within the scope of the disclosure.

What is claimed is:

1. A method of making a bioactive glass fiber comprising: forming a melt of a glass composition comprising:
   50 to 70% $SiO_2$,
   5 to 30% $Na_2O$,
   0.1 to 15% $K_2O$,
   0.1 to 20% CaO, and
   5 to 10% $P_2O_5$, based on a 100 wt % of the glass composition, wherein the melt has a viscosity of from 200 Poise to 2,000 Poise; and
   drawing the melt into a drawn glass fiber;
   wherein the glass composition is free of $Al_2O_3$, MgO, or both.

2. The method of claim 1, wherein the drawn glass fiber has a diameter of from 1 micrometer to 100 micrometers.

3. The method of claim 1, wherein the drawing the melt into the drawn glass fiber is accomplished continuously.

4. The method of claim 1, wherein a temperature of the melt is from 1,050° C. to 1,200° C., and is above a glass liquidus temperature by from 10° C. to 200° C.

5. The method of claim 1, wherein the glass composition comprises:
60 to 70% $SiO_2$,
15 to 30% $Na_2O$,
5 to 15% $K_2O$,
1 to 10% CaO, and
5 to 10% $P_2O_5$, based on a 100 wt % of the glass composition.

6. A bioactive glass composition comprising:
60 to 70% $SiO_2$,
15 to 30% $Na_2O$,
5 to 15% $K_2O$,
1 to 10% CaO, and
5 to 10% $P_2O_5$, based on a 100 wt % of the bioactive glass composition wherein the bioactive glass composition is free of $Al_2O_3$, MgO, or both.

7. The bioactive glass composition of claim 6, further comprising a carrier in an amount of from 5 to 300 wt % by superaddition to the bioactive glass composition to form a bioactive glass formulation.

8. The bioactive glass composition of claim 6, wherein the bioactive glass composition has a biocompatibility of at least one of:
 a proliferation of a live cell line on a surface of the bioactive glass composition; or
 a continuous cell number increase of from 0 to 7 days in proximity of the surface of the bioactive glass composition.

9. The method of claim 1, wherein the glass composition is free of MgO.

10. The method of claim 1, wherein the glass composition is free of $Al_2O_3$.

11. The method of claim 1, wherein the glass composition is free of both $Al_2O_3$ and MgO.

12. The method of claim 1, wherein the glass composition is free of $Al_2O_3$ and comprises 0.1 to 15% MgO, based on a 100 wt % of the glass composition.

13. The method of claim 1, wherein the glass composition is free of MgO and comprises 0.1 to 10% $Al_2O_3$, based on a 100 wt % of the glass composition.

* * * * *